United States Patent
Fischbach

(12) 
(10) Patent No.: US 6,251,437 B1
(45) Date of Patent: Jun. 26, 2001

(54) LIQUID/POWDER ACID CONCENTRATE FOR DIALYSATE AND A METHOD OF MAKING THE SAME

(75) Inventor: LeRoy J. Fischbach, Wayzata, MN (US)

(73) Assignee: Minntech Corporation, Minneapolis, MN (US)

( * ) Notice: Subject to any disclaimer, the term of this patent is extended or adjusted under 35 U.S.C. 154(b) by 0 days.

(21) Appl. No.: 09/352,325

(22) Filed: Jul. 13, 1999

(51) Int. Cl.$^7$ ................................ A61K 9/08; A61K 9/14
(52) U.S. Cl. ................................. 424/489; 514/832
(58) Field of Search ........................ 424/489; 514/832, 514/833

(56) References Cited

U.S. PATENT DOCUMENTS

| | | | |
|---|---|---|---|
| 3,560,380 | 2/1971 | Stade et al. | 252/1 |
| 4,489,535 | 12/1984 | Veltman | 53/431 |
| 4,655,941 | 4/1987 | Suzuki | 252/1 |
| 4,734,198 | 3/1988 | Harm | 210/647 |
| 4,756,838 | 7/1988 | Veltman | 252/1 |
| 4,784,495 | 11/1988 | Jonsson | 366/151 |
| 4,812,239 | 3/1989 | Mills | 210/647 |
| 5,045,324 | 9/1991 | Mukai | 424/678 |
| 5,071,558 | 12/1991 | Itob | 210/542 |
| 5,122,516 | 6/1992 | Watanabe | 514/23 |
| 5,252,213 | 10/1993 | Ahmad | 210/542 |
| 5,295,505 | 3/1994 | Polaschegg | 137/93 |
| 5,318,750 | 6/1994 | Lascombes | 422/81 |
| 5,533,804 | 7/1996 | Larsson | 366/274 |
| 5,540,842 | 7/1996 | Aoyama | 210/647 |

*Primary Examiner*—James M. Spear
(74) *Attorney, Agent, or Firm*—Nixon & Vanderhye PC

(57) ABSTRACT

A hemodialysis acid concentrate which includes, before mixing, sodium chloride powder and sometimes dextrose powder as a powder component, and a liquid component which contains some or all of the following: potassium chloride, magnesium chloride, sodium chloride, dextrose, calcium chloride, and an acid from the group lactic acid, acetic acid, and citric acid. The liquid and powder components are added to a specified volume of water to make a final acid concentrate. The individual components are easily inspected for quality control and the shipping weight is greatly reduced compared to conventional liquid acid concentrates.

32 Claims, No Drawings

LIQUID/POWDER ACID CONCENTRATE FOR DIALYSATE AND A METHOD OF MAKING THE SAME

FIELD OF THE INVENTION

The present invention relates to hemodialysis acid concentrates and more particularly to liquid and powder components used to make various hemodialysis acid concentrates at dialysis facilities for reducing manufacturing and shipping costs and to allow for easily verified quality control.

DEFINITIONS

For clarification, certain terminology used hereinbelow may be defined as follows:

Acid Concentrate (Part "A")—a concentrated aqueous fluid containing electrolytes and usually dextrose, which is intended to be further diluted by the hemodialysis machine with water and part "B" (Bicarbonate Concentrate) to make dialysate. Acid concentrate is usually prepared in one of the following proportioning ratios: 36.83X or 45X.

Bicarbonate Concentrate (Part "B")—a concentrated aqueous fluid containing Sodium Bicarbonate and sometimes Sodium Chloride, which is intended to be further diluted by the hemodialysis machine with water and Part "A" (Acid Concentrate) to make dialysate. Bicarbonate concentrate is usually prepared in one of the following proportioning ratios: 36.83X or 45X. The part "B" concentrate is normally delivered to the dialysis facility as a powder and mixed with water at the facility prior to further dilution by the hemodialysis machine. Bicarbonate concentrate may also be prepared from canisters at the dialysis machine by passing water through a canister which contains sodium bicarbonate powder, to make a saturated solution. (See Jonsson et al. U.S. Pat. No. 4,784,495). Normally the 36.83X concentrate contains Sodium Chloride along with Sodium Bicarbonate. The 45X concentrations normally contain only Sodium Bicarbonate. Ready to use Bicarbonate concentrate is also available but usually is expensive.

Dialysate—an aqueous fluid containing electrolytes and usually dextrose, which is intended to exchange solutes with blood during hemodialysis. "Dialysate" is used throughout this document to mean the fluid delivered to the dialyzer by the hemodialysis machine, made from water, Part "A" concentrate, and Part "B" concentrate.

Hemodialysis Machine—a device that prepares dialysate on line from water, Part "A" concentrate, and Part "B" concentrate; circulates the dialysate through the dialyzer; monitors the dialysate for temperature, conductivity, pressure, flow and blood leaks; and prevents dialysis during disinfection or cleaning modes. The device also monitors the patient's blood flowing through the dialyzer.

BACKGROUND OF INVENTION

Hemodialysis involves the passing of the patient's blood on one side of a porous membrane and a physiological prescription electrolyte solution on the other side of the membrane. Through convection and diffusion the blood is equalized with the electrolyte solution and the patient's blood is cleansed. The membrane is usually part of the hemodialyzer.

The prescription electrolyte is the dialysate. The flow rate of the dialysate is typically 500 ml/min or greater. Thus, a typical 4 hour hemodialysis treatment would require over 30 gallons of dialysate. In a moderate size facility that is treating 25 patients per day, over 750 gallons of this dialysate fluid is required per day. This volume of fluid would present a handling and storage problem. To transport this much fluid every day would be very expensive and present massive logistical problems.

To help solve this problem, the dialysate used to treat patients has been delivered to the dialysis machine in concentrated form and diluted to useable dialysate by the dialysis machine. The standard concentration ratios that have been adapted by the industry for many years are 45X and 36.83X. Acid concentrates (Part A) along with the appropriate bicarbonate concentrate (Part B) is delivered to the hemodialysis machine and the hemodialysis machine further dilutes them with purified water to make the dialysate needed for the hemodialysis treatment. Instead of needing 30 gallons of liquid for each treatment, only three gallons (approx. 1 gallon of Acid concentrate and approx. two gallons of Bicarbonate concentrate) are needed per treatment. This has greatly reduced the cost of shipping, storage, and handling and reduced the logistical problems considerably. It is noted that most of the time the bicarbonate is delivered to the facility as powder and the acid is delivered as liquid.

Depending on the patient's needs, the concentrate is prescribed by the attending physician for that patient. In most dialysis facilities more than one formula is available to treat the patient population. The differences in the formulas may be as minor as a 2 mEq/l change in sodium or as major as a 200 mg/dl change in dextrose in the final dialysate. Most manufactures of acid concentrate offer over 50 different formulas to their customers. Custom formulated acid concentrates may also be offered.

Each hemodialysis patient typically needs to be treated three times per week. As the number of patients receiving hemodialysis has increased (it is estimated that currently over 230,000 patients in the U.S. receive hemodialysis treatments) there is still a large amount of acid concentrate that must be shipped and stored to treat these patients. Thus, concentrating the dialysate 36.83X or 45X has not resolved the problem entirely.

Several potential solutions to this continuing problem have been proposed over the years. First, the acid and bicarbonate concentrates could be made more concentrated. However, this is limited by the solubility of the electrolytes. There are physical limitations as to what volume of chemicals can be put into and maintained in solution. The change from 36.83X to 45X is an example of making the solution more concentrated. The 45X solution is close to this maximum solubility since the maximum amount of sodium chloride which can be placed into solution is about 3.3 lb. per gallon.

Another way of potentially solving this problem is to provide the Acid concentrate or Bicarbonate concentrate as a powder in a canister through which water is pumped. The output of the canister would be a saturated solution which is further diluted by the hemodialysis machine. See, e.g., Jonsson et al. U.S. Pat. No. 4,784,495, which discloses a method using the canister for the bicarbonate concentrate Part "B". Jonsson et al also shows a method to use sodium chloride in a canister. However, it is evident that not all of the electrolytes needed for hemodialysis will dissolve at a sufficient rate to allow the canister process to be used exclusively. Thus, it is necessary to also provide a liquid solution to the machine. Moreover, due to the variation in dissolution rates only one chemical can be used in each canister, which complicates the design of the dialysis machine. This process also needs a special machine to dilute and mix the concentrates.

Another potential solution is to deliver the chemicals to make an acid concentrate in a powder form to the dialysis facility. At the hemodialysis facility, the powder would be reconstituted into acid concentrate by adding water and then supplied to the hemodialysis machine, where it is further diluted with water and Part "B" concentrate to make the dialysate. The powder may be delivered to the facility in large pre-measured quantities which are made up at one time. See, e.g., Harm et al., U.S. Pat. No. 4,734,198. This solution does reduce the shipping cost to an optimal level, but it creates several new problems. Powders in large quantities are heavy and difficult to handle. Moreover, sometimes the powders are slow to dissolve. In addition, the acid required in the formulas is not readily available in powder form and is expensive. Some of the other chemicals used in these powder formulas are also more expensive in powder form. For example, calcium chloride in powder form typically costs $1.88/lb. However, in liquid form calcium chloride can typically cost as low as $0.10/lb.

Lastly, using powder creates multiple mixing steps. When these powders are mixed into solution they are normally added to a starting volume of water and then the solution is topped off with additional water to a fixed final volume. This three step process of filling the tank, adding and mixing the chemicals and topping off requires extra steps which are not desirable for the dialysis facility.

SUMMARY OF THE INVENTION

It is an objective of the invention to simplify the reconstitution of powder and liquid components into an acid concentrate which can be used by the customer in their hemodialysis machines, wherein the finished acid concentrate has the correct formula and is cost effective.

The components of the acid concentrate of the invention are a powder component and a liquid component that are combined with water at the dialysis facility to produce a prescription acid concentrate to meet the patient's needs. The resulting acid concentrate can then be provided to the hemodialysis machine to be further diluted with bicarbonate concentrate and water to make the dialysate.

The powder component of the invention includes sodium chloride and possibly dextrose. The powder sodium chloride and powder dextrose may be packaged together in one package or in separate packages. The powder component may be packaged in a plurality of packages to allow the individual packages to be lighter for easier handling. Since both sodium chloride and dextrose are easily dissolved in water there will be no problem with slow dissolving powders, such as magnesium chloride.

The liquid component of the invention includes the remaining chemicals of the acid concentrate, namely one or more of: potassium chloride, magnesium chloride, calcium chloride, dextrose, sodium chloride and an acid. The acid may be lactic acid, acetic acid, citric acid, or any other physiologically safe acid. Advantageously, the liquid component has a predetermined volume of, for example, about one gallon. The predetermined volume may be one cup (8 fl. oz.) or one liter, particularly for smaller batches, or 2½ gallons for larger batches.

To formulate an acid concentrate, suitable liquid and powder components are selected and added to a fixed volume of water, e.g. 0.5–20 gallons, to make a final volume of acid concentrate.

The invention is also embodied in a method of making an acid concentrate for subsequent dilution with water and a bicarbonate concentrate to produce a dialysate, comprising the steps of providing a powder component consisting essentially of at least one of sodium chloride and dextrose; providing a liquid component comprising at least one of: potassium chloride, magnesium chloride, calcium chloride, dextrose, sodium chloride and an acid; and adding the powder component and the liquid component to a prescribed volume of water, thereby to produce the acid concentrate.

DETAILED DESCRIPTION OF THE INVENTION

According to the invention, a liquid component and a powder component are provided for making acid concentrate used for dialysis. More specifically, the larger quantity raw materials, by volume and weight, are provided in powder form and the smaller quantity raw materials, by volume and weight, are provided to the dialysis facility in liquid form. The powder component of the invention thus consists of sodium chloride, and sometimes dextrose, that is weighed and then placed in a single or multiple bags having the correct amount of chemical for one batch. The quantity of chemical in each bag is determined by the formula of the acid concentrate desired. The powder may be bagged in multiple bags for ease of handling. The weight of the chemicals needed for the formula and the operators ability to handle the package weight will determine the size of the bag.

Advantageously, by leaving only the large quantity chemicals in powder form it is easier to determine if one of the raw materials has inadvertently been omitted. In that regard, by way of example, consider a case the raw materials in the powder container are 24 lb of sodium chloride and 8 lb dextrose. The total weight will be 32 lb. If either the dextrose or the sodium chloride is left out of the package a check weighing of the final package will allow an easy verification that the product is not complete. On the other hand, consider a case where 24 lb of sodium chloride and 8 lb of dextrose are packaged together, plus a minor chemical, for example the potassium chloride which represents only 0.9% of the total package weight. If the potassium chloride were suspected of being left out of the package, there would be no way of readily checking to make this determination. Indeed, the tolerance of the sodium chloride is 2.5% and the potassium chloride (only 0.9%) could easily be hidden within this tolerance.

The liquid component of the invention may include any or all of the following: potassium chloride, magnesium chloride, calcium chloride, sodium chloride, dextrose and an acid. The acid may be lactic acid, acetic acid, citric acid, or any physiologically safe acid. The liquid component is preferably contained in a plastic container and contains concentrations below respective solubility limits. The liquid component with the correct chemicals dissolved into water is preferably brought to a final volume. The final volume of the liquid component will normally be one gallon. Smaller batches may use a liquid volume of about one liter or about one cup (8 fl. oz.), and larger batches may use a liquid volume of about 2½ gallons. A standardized liquid component may be packaged in about 1 gallon containers for addition to 8 gallons of water; 2½ gallon containers for addition to 20 gallons of water; or 8 fl. oz. containers for addition to 0.5 gallons of water. It is possible that other volumes could be used but for consistency in manufacturing and packaging it is most preferred to keep the volume the same. The final volume of the liquid component may be a standard liquid packaging volume such as 21/2 gallons, 1 gallon, 1 liter, 1 quart, 1 pint, 1 cup, 500 ml, ½ gallon, etc. In addition, the final volume of the liquid component may be filled to less than the standard container volume. For example, a one gallon container may contain 0.8 gallons as the final volume.

The smaller volume chemicals are advantageously dissolved into a liquid to make up a large batch of these chemicals. Quality control testing is preferably performed on the batch prior to dispensing into the final container. The liquid can be analyzed, as a batch, using standard chemical test methods such as flame photometer, atomic absorption, etc. By performing the quality control on a large batch of liquid the testing cost is minimized. Because the test methods are standard chemical methods the quality control of these liquids is greatly simplified. The solution can then be dispensed into containers which hold a specified volume.

Advantageously, the quantity of each raw material in the liquid component and powder component will be such that, with the liquid component brought to its final, predetermined volume, and the liquid and powder components are added to a fixed volume of water, the final concentration of each constituent in the resulting acid concentrate will be as specified on the label. By calculating the raw material to be placed into a fixed amount of water the user need only measure the water once. There will be no need to top off the concentrate to the final volume. Thus, when making the acid concentrate a specified amount of water is placed into a container, e.g. about 0.5–20 gallons, more preferably about 6–12 gallons, and most preferably about 8 gallons. The powder component and the liquid component are then added to the water and mixed. The resultant acid concentrate is ready to be provided to a hemodialysis machine for final proportioning with water and the bicarbonate concentrate Part "B". The exact volume of the finished acid concentrate will be determined by the formula (the initial volume of water plus the volume of the liquid and powder components). Thus, the final volume of the concentrate provided in accordance with the invention is dependent on the formula and will typically differ for different formulas. When the concentrations of the electrolytes are higher in one formula than another, the formula with the larger amount of chemicals will produce the largest volume of acid concentrate. For example, the final volume for a SB-100 formula may be 10.996 gallons and the final volume for a SB-1000 formula may be 10.306 gallons.

By removing all or a substantial portion of the large volume solutes (sodium chloride and dextrose) from the liquid acid concentrate and maintaining them in powder form, the liquid component becomes less saturated with solids. By increasing the solids in the liquid component with a higher concentration of the minor solutes, the liquid again becomes highly concentrated. This higher concentration advantageously allows a reduction in the amount of liquid that must be shipped. Indeed, it is estimated that the shipping weight can be reduced by as much as 60%, or more. Since these chemicals are pre-dissolved in a highly concentrated solution there will be no problem with getting these chemicals into solution when they are reconstituted at the dialysis facility to make acid concentrate. This reduction in shipping weight results in a savings to the user by reducing shipping costs. It also reduces storage and handling costs.

To help ensure that the chemical concentration of the invention would work correctly, stability studies were conducted. The stability studies indicate that the amount of chemicals placed into the liquid is stable over time (accelerated studies at 40° C. were used). These studies demonstrate that the proposed invention is functional and that the concentration of solids in the solution will remain stable.

As indicated, some of the sodium chloride and/or dextrose may be added to the liquid. The purpose of doing this is to allow for a standardized powder component that can be used with different liquid components. For example, the sodium chloride in the powder component may be determined by the lowest amount required for any of the formulas to be produced. The balance of the sodium chloride required for the respective formulas is then incorporated in the liquid component for that respective formula. By producing the product in this way, the powder component is standardized and the liquid component will determine the final formula. This minimizes the possibility of a user making a mistake and using the wrong powder component with the liquid component. It will also simplify ordering and storage.

For example, the powder component may contain enough sodium chloride to give 130 mEq/l sodium in the final dialysate along with 200 mg/dl of dextrose. The customer needs 145 mEq/l of sodium in the final dialysate. Thus, 15 mEq/l of sodium is added to the liquid component. The resulting final dialysate will be the necessary 145 mEq/l of sodium.

Below is a listing of the normally used solute ranges in dialysates

|  | Range | SB-1XXX Formula |
| --- | --- | --- |
| Sodium | 126–145 mEq/ml | 140 mEq/l |
| Potassium | 0–3.5 mEq/ml | 2 mEq/l |
| Calcium | 0–4.0 mEq/ml | 3 mEq/l |
| Magnesium | 0.5–1.5 mEq/ml | 1 mEq/l |
| Chloride | 100–112 mEq/ml | 100 mEq/l |
| Dextrose | 0–300 mg/dl | 200 mg/dl |

Below is a chart showing exemplary ranges of the chemicals to achieve various formulas of the "Part A" acid concentrate in accordance with the invention, specific examples of which are included in the following Tables 1–21, summarized more particularly herein below.

| "Part A" Acid Concentrate | | | | |
| --- | --- | --- | --- | --- |
|  |  |  | Specific formula as concentrate | |
| Chemical | gm/l | lb/gal | SB-1020 gm/l | SB-119 gm/l |
| Sodium Chloride | 153–289 | 1.28–3.0 | 172.2 | 263 |
| Calcium Chloride | 0.0–13.0 | 0.0–0.09 | 6.8 | 9.9 |
| Potassium Chloride | 0.0–12.0 | 0.0–0.05 | 5.5 | 3.4 |
| Magnesium Chloride | 1.0–8.0 | 0.02–0.08 | 3.7 | 3.4 |
| Acetic Acid | 7–12 | 0.065–0.1 | 8.8 | 10.8 |
| Dextrose | 0.0–150 | 0.0–1.1 | 72.7 | 90 |

Exemplary powder and liquid components provided in accordance with the invention for being mixed with a prescribed amount of water to produce an acid concentrate of a prescribed formula are listed below in TABLES 1–21.

In the presently preferred embodiments, as noted above and as detailed below in TABLES 1–7, the starting water volume is 8 gallons. The chemicals have thus been calculated to produce a final concentrate with this starting water. In each of the examples of TABLES 1–7, the powder component, which in these examples consists of sodium chloride and dextrose, is provided in one or more sealed bags for storage and transport. The liquid component is formulated to bring its total volume up to one gallon. There is nothing to restrict changing the starting water to another level, or producing the liquid component in another size, e.g. less than 1 gallon, as long as the solubility is within physical limits, and the final concentrate formula is met.

Further examples of quantities of liquid and powder components provided in accordance with the invention for being mixed with a prescribed amount of water to produce an acid concentrate of a prescribed formula are listed below in Tables 8–14. In the examples of Tables 8–14, the liquid components and powder component(s) are calculated so that when they are mixed with water at a starting water volume of 0.60 gallons they yield a final acid concentrate volume of approximately one gallon. The chemicals have thus been calculated to produce a final concentrate with this starting water. In each of the examples of Tables 8–14, the powder component, which in these examples consists of sodium chloride and dextrose, is provided in one or more sealed bags for storage and transport. In these examples, the liquid component is formulated to bring its total volume up to one quart. More specifically, in the examples given in Tables 8–14, the chemicals in the liquid component are calcium chloride, magnesium chloride, potassium chloride, acetic acid and are brought to a final volume of one quart with water. There is, however, nothing to restrict changing the starting water to another level, or producing the liquid component in another size as long as the solubility is within physical limits. This is demonstrated by a comparison of the examples of Tables 1–7 with the examples of Tables 8–14.

Additional examples of quantities of liquid and powder components provided in accordance with the invention for being mixed with a prescribed amount of water to produce an acid concentrate of a prescribed formula are listed below in Tables 15–21 In the examples of Tables 15–21, the liquid components and powder component(s) are calculated so that when they are mixed with water at a starting water volume of 8 gallons they yield a final acid concentrate volume of approximately ten gallons. The chemicals have thus been calculated to produce a final concentrate with this starting water. As in the examples discussed herein above, the powder component, which in these examples consists of sodium chloride and dextrose, is provided in one or more sealed bags for storage and transport. In contrast to the above described embodiments, the powder component is the same or standardized for two or more of the formulations even though the final concentration of sodium chloride and/or dextrose may differ. That is, the powder component is the same for each of two or more of the formulas. In these examples, two (2) standard formulas are provided, one exemplified by Tables 15–16 and the other exemplified by Tables 17–21. Two standard formulas are provided because of the great difference in sodium chloride between the respective formulas. One formula is for 45X concentrates and the other is for 36.83X concentrates. The liquid component is formulated to bring its total volume up to one gallon. In this example, the liquid component is formulated with sodium chloride as one of the components, since the powder component gives a standard 170 gm/l. Thus, the amount of sodium chloride in the liquid component is calculated to bring the total sodium to the amount prescribed in the final concentrate formula. Again, there is nothing to restrict changing the starting water to another level, or producing the liquid component in another size as long as the solubility is within physical limits.

TABLE 1

SB-100

| Material | Desired Final Conc. (gm/L) | Desired Starting Vol Gallons |
|---|---|---|
| NaCl | 268.2 | — |
| CaCl(2) | 9.924 | — |
| KCl | 5.033 | — |
| MgCl(2) | 4.574 | — |
| Acetic Acid | 10.8 | — |
| Dextrose | 90 | — |
| Water | — | 8 |

| | Quantities Needed for Desired Starting Volume | |
|---|---|---|
| Material | Solids (gm) | Liquid Gallon (gm) |
| NaCl | 11147.3984 | — |
| CaCl(2) | — | 412.4787 |
| KCl | — | 209.1904 |
| MgCl(2) | — | 190.1126 |
| Acetic Acid | — | 448.8885 |
| Dextrose | 3740.7377 | — |

| | Quantities Needed for Desired Starting Volume | |
|---|---|---|
| Material | Solids (lbs) | Liquid Gallon (lbs) |
| NaCl | 24.55 | — |
| CaCl(2) | — | 0.91 |
| KCl | — | 0.46 |
| MgCl(2) | — | 0.42 |
| Acetic Acid | — | 0.99 |
| Dextrose | 8.24 | — |
| Total Wt. | 32.79 | 2.78 |
| Total Final Vol. | 10.9957 Gallons | |

TABLE 2

SB-119

| Material | Desired Final Conc. (gm/L) | Desired Starting Vol Gallons |
|---|---|---|
| NaCl | 263 | — |
| CaCl(2) | 9.9 | — |
| KCl | 3.4 | — |
| MgCl(2) | 3.4 | — |
| Acetic Acid | 10.8 | — |
| Dextrose | 90 | — |
| Water | — | 8 |

| | Quantities Needed for Desired Starting Volume | |
|---|---|---|
| Material | Solids (gm) | Liquid Gallon (gm) |
| NaCl | 10899.2835 | — |
| CaCl(2) | — | 410.2772 |
| KCl | — | 140.9033 |
| MgCl(2) | — | 140.9033 |
| Acetic Acid | — | 447.5751 |
| Dextrose | 3729.7928 | — |

| | Quantities Needed for Desired Starting Volume | |
|---|---|---|
| Material | Solids (lbs) | Liquid Gallon (lbs) |
| NaCl | 24.01 | — |
| CaCl(2) | — | 0.90 |
| KCl | — | 0.31 |
| MgCl(2) | — | 0.31 |

TABLE 2-continued

SB-119

| | | |
|---|---|---|
| Acetic Acid | — | 0.99 |
| Dextrose | 8.22 | — |
| Total Wt. | 32.22 | 2.51 |
| Total Final Vol. | 10.9635 Gallons | |

TABLE 3

SB-1000

| Material | Desired Final Conc. (gm/L) | Desired Starting Vol Gallons |
|---|---|---|
| NaCl | 172.2 | — |
| CaCl(2) | 0 | — |
| KCl | 5.492 | — |
| MgCl(2) | 3.744 | — |
| Acetic Acid | 8.8 | — |
| Dextrose | 73.66 | — |
| Water | — | 8 |

Quantities Needed for Desired Starting Volume

| Material | Solids (gm) | Liquid Gallon (gm) |
|---|---|---|
| NaCl | 6708.1352 | — |
| CaCl(2) | — | 0.0000 |
| KCl | — | 213.9435 |
| MgCl(2) | — | 145.8494 |
| Acetic Acid | — | 342.8083 |
| Dextrose | 2869.4613 | — |

Quantities Needed for Desired Starting Volume

| Material | Solids (lbs) | Liquid Gallon (lbs) |
|---|---|---|
| NaCl | 14.78 | — |
| CaCl(2) | — | 0.00 |
| KCl | — | 0.47 |
| MgCl(2) | — | 0.32 |
| Acetic Acid | — | 0.76 |
| Dextrose | 6.32 | — |
| Total Wt. | 21.10 | 1.55 |
| Total Final Vol. | 10.3057 Gallons | |

TABLE 4

SB-1003

| Material | Desired Final Conc. (gm/L) | Desired Starting Vol Gallons |
|---|---|---|
| NaCl | 172.3 | — |
| CaCl(2) | 9.476 | — |
| KCl | 5.492 | — |
| MgCl(2) | 3.744 | — |
| Acetic Acid | 8.847 | — |
| Dextrose | 73.66 | — |
| Water | — | 8 |

Quantities Needed for Desired Starting Volume

| Material | Solids (gm) | Liquid Gallon (gm) |
|---|---|---|
| NaCl | 6712.3858 | — |
| CaCl(2) | — | 369.1617 |
| KCl | — | 213.9549 |
| MgCl(2) | — | 145.8571 |

TABLE 4-continued

SB-1003

| | | |
|---|---|---|
| Acetic Acid | — | 344.6574 |
| Dextrose | 2869.6131 | — |

Quantities Needed for Desired Starting Volume

| Material | Solids (lbs) | Liquid Gallon (lbs) |
|---|---|---|
| NaCl | 14.78 | — |
| CaCl(2) | — | 0.81 |
| KCl | — | 0.47 |
| MgCl(2) | — | 0.32 |
| Acetic Acid | — | 0.76 |
| Dextrose | 6.32 | — |
| Total Wt. | 21.11 | 2.36 |
| Total Final Vol. | 10.3062 Gallons | |

TABLE 5

SB-1019

| Material | Desired Final Conc. (gm/L) | Desired Starting Vol Gallons |
|---|---|---|
| NaCl | 172.2 | — |
| CaCl(2) | 8.122 | — |
| KCl | 5.492 | — |
| MgCl(2) | 3.744 | — |
| Acetic Acid | 8.846 | — |
| Dextrose | 73.66 | — |
| Water | — | 8 |

Quantities Needed for Desired Starting Volume

| Material | Solids (gm) | Liquid Gallon (gm) |
|---|---|---|
| NaCl | 6708.1352 | — |
| CaCl(2) | — | 316.3965 |
| KCl | — | 213.9435 |
| MgCl(2) | — | 145.8494 |
| Acetic Acid | — | 344.6003 |
| Dextrose | 2869.4613 | — |

Quantities Needed for Desired Starting Volume

| Material | Solids (lbs) | Liquid Gallon (lbs) |
|---|---|---|
| NaCl | 14.78 | — |
| CaCl(2) | — | 0.70 |
| KCl | — | 0.47 |
| MgCl(2) | — | 0.32 |
| Acetic Acid | — | 0.76 |
| Dextrose | 6.32 | — |
| Total Wt. | 21.10 | 2.25 |
| Total Final Vol. | 10.3057 Gallons | |

TABLE 6

SB-1020

| Material | Desired Final Conc. (gm/L) | Desired Starting Vol Gallons |
|---|---|---|
| NaCl | 172.2 | — |
| CaCl(2) | 6.768 | — |
| KCl | 5.492 | — |
| MgCl(2) | 3.744 | — |
| Acetic Acid | 8.847 | — |

TABLE 6-continued

SB-1020

| Material | | |
|---|---|---|
| Dextrose | 73.66 | — |
| Water | — | 8 |

| | Quantities Needed for Desired Starting Volume | |
|---|---|---|
| Material | Solids (gm) | Liquid Gallon (gm) |
| NaCl | 6708.1352 | — |
| CaCl(2) | — | 263.6507 |
| KCl | — | 213.9435 |
| MgCl(2) | — | 145.8494 |
| Acetic Acid | — | 344.6392 |
| Dextrose | 2869.4613 | — |

| | Quantities Needed for Desired Starting Volume | |
|---|---|---|
| Material | Solids (lbs) | Liquid Gallon (lbs) |
| NaCl | 14.78 | — |
| CaCl(2) | — | 0.58 |
| KCl | — | 0.47 |
| MgCl(2) | — | 0.32 |
| Acetic Acid | — | 0.76 |
| Dextrose | 6.32 | — |
| Total Wt. | 21.10 | 2.13 |
| Total Final Vol. | 10.3057 Gallons | |

TABLE 7

SB-1080

| Material | Desired Final Conc. (gm/L) | Desired Starting Vol Gallons |
|---|---|---|
| NaCl | 174.2 | — |
| CaCl(2) | 8.122 | — |
| KCl | 2.746 | — |
| MgCl(2) | 3.744 | — |
| Acetic Acid | 8.847 | — |
| Dextrose | 73.66 | — |
| Water | — | 8 |

| | Quantities Needed for Desired Starting Volume | |
|---|---|---|
| Material | Solids (gm) | Liquid Gallon (gm) |
| NaCl | 6793.2321 | — |
| CaCl(2) | — | 316.7315 |
| KCl | — | 107.0850 |
| MgCl(2) | — | 146.0038 |
| Acetic Acid | — | 345.0042 |
| Dextrose | 2872.4999 | — |

| | Quantities Needed for Desired Starting Volume | |
|---|---|---|
| Material | Solids (lbs) | Liquid Gallon (lbs) |
| NaCl | 14.96 | — |
| CaCl(2) | — | 0.70 |
| KCl | — | 0.24 |
| MgCl(2) | — | 0.32 |
| Acetic Acid | — | 0.76 |
| Dextrose | 6.33 | — |
| Total Wt. | 21.29 | 2.02 |
| Total Final Vol. | 10.3166 Gallons | |

TABLE 8

SB-100

| Material | Desired Final Conc. (gm/L) | Desired Starting Vol Gallons |
|---|---|---|
| NaCl | 268.2 | — |
| CaCl(2) | 9.924 | — |
| KCl | 5.033 | — |
| MgCl(2) | 4.574 | — |
| Acetic Acid | 10.8 | — |
| Dextrose | 90 | — |
| Water | — | 0.6 |

| | Quantities Needed for Desired Starting Volume | |
|---|---|---|
| Material | Solids (gm) | Liquid Quart (gm) |
| NaCl | 1052.8098 | — |
| CaCl(2) | — | 38.9563 |
| KCl | — | 19.7569 |
| MgCl(2) | — | 17.9551 |
| Acetic Acid | — | 42.3950 |
| Dextrose | 353.2919 | — |

| | Quantities Needed for Desired Starting Volume | |
|---|---|---|
| Material | Solids (lbs) | Liquid Quart (lbs) |
| NaCl | 2.32 | — |
| CaCl(2) | — | 0.09 |
| KCl | — | 0.04 |
| MgCl(2) | — | 0.04 |
| Acetic Acid | — | 0.09 |
| Dextrose | 0.78 | — |
| Total Wt. | 3.10 | 0.26 |
| Total Final Vol. | 1.0385 Gallons | |

TABLE 9

SB-119

| Material | Desired Final Conc. (gm/L) | Desired Starting Vol Gallons |
|---|---|---|
| NaCl | 263 | — |
| CaCl(2) | 9.9 | — |
| KCl | 3.4 | — |
| MgCl(2) | 3.4 | — |
| Acetic Acid | 10.8 | — |
| Dextrose | 90 | — |
| Water | — | 0.6 |

| | Quantities Needed for Desired Starting Volume | |
|---|---|---|
| Material | Solids (gm) | Liquid Quart (gm) |
| NaCl | 1029.3768 | — |
| CaCl(2) | — | 38.7484 |
| KCl | — | 13.3075 |
| MgCl(2) | — | 13.3075 |
| Acetic Acid | — | 42.2710 |
| Dextrose | 352.2582 | — |

| | Quantities Needed for Desired Starting Volume | |
|---|---|---|
| Material | Solids (lbs) | Liquid Quart (lbs) |
| NaCl | 2.27 | — |
| CaCl(2) | — | 0.09 |
| KCl | — | 0.03 |
| MgCl(2) | — | 0.03 |

TABLE 9-continued

SB-119

| Acetic Acid | — | 0.09 |
|---|---|---|
| Dextrose | 0.78 | — |
| Total Wt. | 3.04 | 0.24 |
| Total Final Vol. | 1.0354 Gallons | |

TABLE 10

SB-1000

| Material | Desired Final Conc. (gm/L) | Desired Starting Vol Gallons |
|---|---|---|
| NaCl | 172.2 | — |
| CaCl(2) | 0 | — |
| KCl | 5.492 | — |
| MgCl(2) | 3.744 | — |
| Acetic Acid | 8.8 | — |
| Dextrose | 73.66 | — |
| Water | — | 0.6 |

Quantities Needed for Desired Starting Volume

| Material | Solids (gm) | Liquid Quart (gm) |
|---|---|---|
| NaCl | 633.5461 | — |
| CaCl(2) | — | 0.0000 |
| KCl | — | 20.2058 |
| MgCl(2) | — | 13.7747 |
| Acetic Acid | — | 32.3763 |
| Dextrose | 271.0047 | — |

Quantities Needed for Desired Starting Volume

| Material | Solids (lbs) | Liquid Quart (lbs) |
|---|---|---|
| NaCl | 1.40 | — |
| CaCl(2) | — | 0.00 |
| KCl | — | 0.04 |
| MgCl(2) | — | 0.03 |
| Acetic Acid | — | 0.07 |
| Dextrose | 0.60 | — |
| Total Wt. | 1.99 | 0.15 |
| Total Final Vol. | 0.9733 Gallons | |

TABLE 11

SB-1003

| Material | Desired Final Conc. (gm/L) | Desired Starting Vol Gallons |
|---|---|---|
| NaCl | 172.3 | — |
| CaCl(2) | 9.476 | — |
| KCl | 5.492 | — |
| MgCl(2) | 3.744 | — |
| Acetic Acid | 8.847 | — |
| Dextrose | 73.66 | — |
| Water | — | 0.6 |

Quantities Needed for Desired Starting Volume

| Material | Solids (gm) | Liquid Quart (gm) |
|---|---|---|
| NaCl | 633.9475 | — |
| CaCl(2) | — | 34.8653 |
| KCl | — | 20.2068 |
| MgCl(2) | — | 13.7754 |

TABLE 11-continued

SB-1003

| Acetic Acid | — | 32.5510 |
|---|---|---|
| Dextrose | 271.0190 | — |

Quantities Needed for Desired Starting Volume

| Material | Solids (lbs) | Liquid Quart (lbs) |
|---|---|---|
| NaCl | 1.40 | — |
| CaCl(2) | — | 0.08 |
| KCl | — | 0.04 |
| MgCl(2) | — | 0.03 |
| Acetic Acid | — | 0.07 |
| Dextrose | 0.60 | — |
| Total Wt. | 1.99 | 0.22 |
| Total Final Vol. | 0.9734 Gallons | |

TABLE 12

SB-1019

| Material | Desired Final Conc. (gm/L) | Desired Starting Vol Gallons |
|---|---|---|
| NaCl | 172.2 | — |
| CaCl(2) | 8.122 | — |
| KCl | 5.492 | — |
| MgCl(2) | 3.744 | — |
| Acetic Acid | 8.846 | — |
| Dextrose | 73.66 | — |
| Water | — | 0.6 |

Quantities Needed for Desired Starting Volume

| Material | Solids (gm) | Liquid Quart (gm) |
|---|---|---|
| NaCl | 633.5461 | — |
| CaCl(2) | — | 29.8819 |
| KCl | — | 20.2058 |
| MgCl(2) | — | 13.7747 |
| Acetic Acid | — | 32.5456 |
| Dextrose | 271.0047 | — |

Quantities Needed for Desired Starting Volume

| Material | Solids (lbs) | Liquid Quart (lbs) |
|---|---|---|
| NaCl | 1.40 | — |
| CaCl(2) | — | 0.07 |
| KCl | — | 0.04 |
| MgCl(2) | — | 0.03 |
| Acetic Acid | — | 0.07 |
| Dextrose | 0.60 | — |
| Total Wt. | 1.99 | 0.21 |
| Total Final Vol. | 0.9733 Gallons | |

TABLE 13

SB-1020

| | | | | Quantities Needed for Desired Starting Volume | |
|---|---|---|---|---|---|
| Material | Desired Final Conc. (gm/L) | Desired Starting Vol Gallons | Material | Solids (gm) | Liquid Quart (gm) |
| NaCl | 172.2 | — | NaCl | 633.5461 | — |
| CaCl(2) | 6.768 | — | CaCl(2) | — | 24.9003 |
| KCl | 5.492 | — | KCl | — | 20.2058 |
| MgCl(2) | 3.744 | — | MgCl(2) | — | 13.7747 |
| Acetic Aci | 8.847 | — | Acetic Acid | — | 32.5493 |
| Dextrose | 73.66 | — | Dextrose | 271.0047 | — |
| Water | — | 0.6 | NaCl | 1.40 | — |
| | | | CaCl(2) | — | 0.05 |
| | | | KCl | — | 0.04 |
| | | | MgCl(2) | — | 0.03 |
| | | | Acetic Acid | — | 0.07 |
| | | | Dextrose | 0.60 | — |
| | | | Total Wt. | 1.99 | 0.20 |
| | | | Total Final Vol. | 0.9733 Gallons | |

TABLE 14

SB-1080

| | | | | Quantities Needed for Desired Starting Volume | |
|---|---|---|---|---|---|
| Material | Desired Final Conc. (gm/L) | Desired Starting Vol Gallons | Material | Solids (gm) | Liquid Quart (gm) |
| NaCl | 174.2 | — | NaCl | 641.5830 | — |
| CaCl(2) | 8.122 | — | CaCl(2) | — | 29.9135 |
| KCl | 2.746 | — | KCl | — | 10.1136 |
| MgCl(2) | 3.744 | — | MgCl(2) | — | 13.7892 |
| Acetic Acid | 8.847 | — | Acetic Acid | — | 32.5837 |
| Dextrose | 73.66 | — | Dextrose | 271.2917 | — |
| Water | — | 0.6 | NaCl | 1.41 | — |
| | | | CaCl(2) | — | 0.07 |
| | | | KCl | — | 0.02 |
| | | | MgCl(2) | — | 0.03 |
| | | | Acetic Acid | — | 0.07 |
| | | | Dextrose | 0.60 | — |
| | | | Total Wt. | 2.01 | 0.19 |
| | | | Total Final Vol. | 0.9743 Gallons | |

TABLE 15

SB-100

| | | | | Quantities Needed for Desired Starting Volume | |
|---|---|---|---|---|---|
| Material | Desired Final Conc. (gm/L) | Desired Starting Vol Gallons | Material | Solids (gm) | Liquid Quart (gm) |
| NaCl | 268.2 | — | NaCl | 10756.7997 | 339.2529 |
| CaCl(2) | 9.924 | — | CaCl(2) | — | 410.5788 |
| KCl | 5.033 | — | KCl | — | 208.2268 |
| MgCl(2) | 4.574 | — | MgCl(2) | — | 189.2369 |
| Acetic Acid | 10.8 | — | Acetic Acid | — | 446.8209 |
| Dextrose | 90 | — | Dextrose | 3723.5076 | — |
| Water | — | 8 | Total Final Vol. | 41.3723 | Liters |
| | | | NaCl | 23.69 | 0.75 |
| | | | CaCl(2) | — | 0.90 |
| | | | KCl | — | 0.46 |
| | | | MgCl(2) | — | 0.42 |
| | | | Acetic Acid | — | 0.98 |

TABLE 15-continued

SB-100

| Material | Desired Final Conc. (gm/L) | Desired Starting Vol Gallons | Material | Solids (gm) | Liquid Quart (gm) |
|---|---|---|---|---|---|
| | | | Dextrose | 8.20 | — |
| | | | Total Wt. | 31.89 | 3.51 |
| | | | Total Final Vol. | 10.9451 Gallons | |

STANDARD #1--45X
SODIUN FROM POWDER = 260 gm/l
SODIUM FROM LIQUID = 8.2 gm/l

TABLE 16

SB-119

| Material | Desired Final Conc. (gm/L) | Desired Starting Vol Gallons | Material | Solids (gm) | Liquid Quart (gm) |
|---|---|---|---|---|---|
| NaCl | 263 | — | NaCl | 10756.7997 | 124.1169 |
| CaCl(2) | 9.9 | — | CaCl(2) | — | 409.5858 |
| KCl | 3.4 | — | KCl | — | 140.6658 |
| MgCl(2) | 3.4 | — | MgCl(2) | — | 140.6658 |
| Acetic Acid | 10.8 | — | Acetic Acid | — | 446.8209 |
| Dextrose | 90 | — | Dextrose | 3723.5076 | — |
| Water | — | 8 | Total Final Vol. | 41.3723 | Liters |
| | | | NaCl | 23.69 | 0.27 |
| | | | CaCl(2) | — | 0.90 |
| | | | KCl | — | 0.31 |
| | | | MgCl(2) | — | 0.31 |
| | | | Acetic Acid | — | 0.98 |
| | | | Dextrose | 8.20 | — |
| | | | Totat Wt. | 31.89 | 2.78 |
| | | | Total Final Vol. | 10.9451 Gallons | |

STANDARD #1--45X
SODIUM FROM POWDER = 260 gm/l
SODIUM FROM LIQUID = 3 gm/l

TABLE 17

SB-1000

| Material | Desired Final Conc. (gm/L) | Desired Starting Vol Gallons |
|---|---|---|
| NaCl | 172.2 | — |
| CaCl(2) | 0 | — |
| KCl | 5.492 | — |
| MgCl(2) | 3.744 | — |
| Acetic Acid | 8.8 | — |
| Dextrose | 73.66 | — |
| Water | — | 8 |

Quantities Needed for Desired Starting Volume

| Material | Solids (gm) | Liquid Gallon (gm) |
|---|---|---|
| NaCl | 6614.7363 | 85.6025 |
| CaCl(2) | — | 0.0000 |
| KCl | — | 213.6949 |
| MgCl(2) | — | 145.6798 |
| Acetic Acid | — | 342.4099 |
| Dextrose | 2866.1263 | — |
| Total Final Vol. | | 38.9102 Liters |

TABLE 17-continued

SB-1000

Quantities Needed for Desired Starting Volume

| Material | Solids (lbs) | Liquid Gallon (lbs) |
|---|---|---|
| NaCl | 14.57 | 0.19 |
| CaCl(2) | — | 0.00 |
| KCl | — | 0.47 |
| MgCl(2) | — | 0.32 |
| Acetic Acid | — | 0.75 |
| Dextrose | 6.31 | — |
| Total Wt. | 20.88 | 1.73 |
| Total Final Vol. | | 10.2937 Gallons |

STANDARD #2---36.83X
SODIUM FROM POWDER = 170 gm/l
SODIUM FROM LIQUID = 2.2 gm/l

TABLE 18

SB-1003

| Material | Desired Final Conc. (gm/L) | Desired Starting Vol Gallons |
|---|---|---|
| NaCl | 172.3 | — |
| CaCl(2) | 9.476 | — |
| KCl | 5.492 | — |
| MgCl(2) | 3.744 | — |
| Acetic Acid | 8.847 | — |
| Dextrose | 73.66 | — |
| Water | — | 8 |

| | Quantities Needed for Desired Starting Volume | |
|---|---|---|
| Material | Solids (gm) | Liquid Gallon (gm) |
| NaCl | 6614.7363 | 89.4935 |
| CaCl(2) | — | 368.7132 |
| KCl | — | 213.6949 |
| MgCl(2) | — | 145.6798 |
| Acetic Acid | — | 344.2387 |
| Dextrose | 2866.1263 | — |
| Total Final Vol. | | 38.9102 Liters |

| | Quantities Needed for Desired Starting Volume | |
|---|---|---|
| Material | Solids (lbs) | Liquid Gallon (lbs) |
| NaCl | 14.57 | 0.20 |
| CaCl(2) | — | 0.81 |
| KCl | — | 0.47 |
| MgCl(2) | — | 0.32 |
| Acetic Acid | — | 0.76 |
| Dextrose | 6.31 | — |
| Total Wt. | 20.88 | 2.56 |
| Total Final Vol. | | 10.2937 Gallons |

STANDARD #2---36.83X
SODIUM FROM POWDER = 170 gm/l
SODIUM FROM LIQUID = 2.3 gm/l

TABLE 19

SB-1019

| Material | Desired Final Conc. (gm/L) | Desired Starting Vol Gallons |
|---|---|---|
| NaCl | 172.2 | — |
| CaCl(2) | 8.122 | — |
| KCl | 5.492 | — |
| MgCl(2) | 3.744 | — |
| Acetic Acid | 8.846 | — |
| Dextrose | 73.66 | — |
| Water | — | 8 |

| | Quantities Needed for Desired Starting Volume | |
|---|---|---|
| Material | Solids (gm) | Liquid Gallon (gm) |
| NaCl | 6614.7363 | 85.6025 |
| CaCl(2) | — | 316.0288 |
| KCl | — | 213.6949 |
| MgCl(2) | — | 145.6798 |
| Acetic Acid | — | 344.1997 |
| Dextrose | 2866.1263 | — |
| Total Final Vol. | | 38.9102 Liters |

TABLE 19-continued

SB-1019

| | Quantities Needed for Desired Starting Volume | |
|---|---|---|
| Material | Solids (lbs) | Liquid Gallon (lbs) |
| NaCl | 14.57 | 0.19 |
| CaCl(2) | — | 0.70 |
| KCl | — | 0.47 |
| MgCl(2) | — | 0.32 |
| Acetic Acid | — | 0.76 |
| Dextrose | 6.31 | — |
| Total Wt. | 20.88 | 2.43 |
| Total Final Vol. | | 10.2937 Gallons |

STANDARD #2---36.83X
SODIUM FROM POWDER = 170 gm/l
SODIUM FROM LIQUID = 2.2 gm/l

TABLE 20

SB-1020

| Material | Desired Final Conc. (gm/L) | Desired Starting Vol Gallons |
|---|---|---|
| NaCl | 172.2 | — |
| CaCl(2) | 6.768 | — |
| KCl | 5.492 | — |
| MgCl(2) | 3.744 | — |
| Acetic Acid | 8.847 | — |
| Dextrose | 73.66 | — |
| Water | — | 8 |

| | Quantities Needed for Desired Starting Volume | |
|---|---|---|
| Material | Solids (gm) | Liquid Gallon (gm) |
| NaCl | 6614.7363 | 85.6025 |
| CaCl(2) | — | 263.3443 |
| KCl | — | 213.6949 |
| MgCl(2) | — | 145.6798 |
| Acetic Acid | — | 344.2387 |
| Dextrose | 2866.1263 | — |
| Total Final Vol. | | 38.9102 Liters |

| | Quantities Needed for Desired Starting Volume | |
|---|---|---|
| Material | Solids (lbs) | Liquid Gallon (lbs) |
| NaCl | 14.57 | 0.19 |
| CaCl(2) | — | 0.58 |
| KCl | — | 0.47 |
| MgCl(2) | — | 0.32 |
| Acetic Acid | — | 0.76 |
| Dextrose | 6.31 | — |
| Total Wt. | 20.88 | 2.32 |
| Total Final Vol. | | 10.2937 Gallons |

STANDARD #2---36.83X
SODIUM FROM POWDER = 170 gm/l
SODIUM FROM LIQUID = 2.2 gm/l

TABLE 21

SB-1080

| Material | Desired Final Conc. (gm/L) | Desired Starting Vol Gallons |
|---|---|---|
| NaCl | 174.2 | — |
| CaCl(2) | 8.122 | — |
| KCl | 2.746 | — |

TABLE 21-continued

SB-1080

| | | |
|---|---|---|
| MgCl(2) | 3.744 | — |
| Acetic Acid | 8.847 | — |
| Dextrose | 73.66 | — |
| Water | — | 8 |

Quantities Needed for Desired Starting Volume

| Material | Solids (gm) | Liquid Gallon (gm) |
|---|---|---|
| NaCl | 6614.7363 | 163.4229 |
| CaCl(2) | — | 316.0288 |
| KCl | — | 106.8474 |
| MgCl(2) | — | 145.6798 |
| Acetic Acid | — | 344.2387 |
| Dextrose | 2866.1263 | — |
| Total Final Vol. | | 38.9102 Liters |

Quantities Needed for Desired Starting Volume

| Material | Solids (lbs) | Liquid Gallon (lbs) |
|---|---|---|
| NaCl | 14.57 | 0.36 |
| CaCl(2) | — | 0.70 |
| KCl | — | 0.24 |
| MgCl(2) | — | 0.32 |
| Acetic Acid | — | 0.76 |
| Dextrose | 6.31 | — |
| Total Wt. | 20.88 | 2.37 |
| Total Final Vol. | | 10.2937 Gallons |

STANDARD #2---36.83X
SODIUM FROM POWDER = 170 gm/l
SODIUM FROM LIQUID = 2.2 gm/l

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed:

1. A hemodialysis acid concentrate comprising the following components before mixing with water:
   a powder component consisting essentially of at least one of sodium chloride and dextrose; and
   a liquid component comprising at least one of: potassium chloride, magnesium chloride, calcium chloride, dextrose, sodium chloride and an acid.

2. A hemodialysis concentrate as in claim 1, wherein the liquid component includes an acid selected from the group consisting of: lactic acid, acetic acid and citric acid.

3. A hemodialysis acid concentrate as in claim 1, wherein the powder component consists essentially of sodium chloride and dextrose.

4. A hemodialysis acid concentrate as in claim 1, wherein said liquid and powder components are mixed with a prescribed volume of water to make a final volume of acid concentrate solution.

5. A hemodialysis acid concentrate as in claim 4, wherein sodium chloride is provided in a quantity to provide a final concentration in said final volume of acid concentrate solution of between about 153–289 gm/l.

6. A hemodialysis acid concentrate as in claim 4, wherein the calcium chloride is provided in a quantity to provide a final concentration in said final volume of acid concentrate solution of between about 0.0–13.0 gm/l.

7. A hemodialysis acid concentrate as in claim 4, wherein the potassium chloride is provided in a quantity to provide a final concentration in said final volume of acid concentrate solution of between about 0.0–12.0 gm/l.

8. A hemodialysis acid concentrate as in claim 4, wherein the magnesium chloride is provided in a quantity to provide a final concentration in said final volume of acid concentrate solution of between about 1.0–8.0 gm/l.

9. A hemodialysis acid concentrate as in claim 4, wherein dextrose is provided in a quantity to provide a final concentration in said final volume of acid concentrate solution of between about 0.0–150 gm/l.

10. A hemodialysis acid concentrate as in claim 4, wherein the acid of the liquid component is acetic acid, said acetic acid being provided in a quantity sufficient to provide a final concentration in said final volume of acid concentrate solution of between about 7–12 gm/l.

11. A hemodialysis acid concentrate as in claim 4, wherein the prescribed volume of water is between about 0.5 and 20 gallons.

12. A hemodialysis acid concentrate according to claim 1, wherein the volume of the liquid component is between about one cup and about 2½ gallons.

13. A hemodialysis acid concentrate according to claim 12, wherein the volume of the liquid component is a standard liquid packaging volume.

14. A hemodialysis acid concentrate according to claim 1, wherein the volume of the liquid component is less than about one gallon.

15. A hemodialysis acid concentrate consisting essentially of the following before mixing with water:
   (a) powdered dextrose;
   (b) powdered sodium chloride; and
   (c) a liquid component comprising potassium chloride; magnesium chloride; calcium chloride; an acid; and water.

16. A hemodialysis acid concentrate as in claim 15, wherein the liquid component includes an acid selected from the group consisting of: lactic acid, acetic acid and citric acid.

17. A hemodialysis acid concentrate according to claim 15, wherein the volume of the liquid component is about one gallon.

18. A hemodialysis acid concentrate according to claim 15, further comprising a prescribed volume of water to which the dextrose, the sodium chloride, and the liquid component are added to make an acid concentrate solution.

19. A hemodialysis acid concentrate according to claim 18, wherein said prescribed volume is about 0.5–20 gallons of water.

20. A hemodialysis acid concentrate according to claim 19, wherein said prescribed volume is about 6–12 gallons of water.

21. A hemodialysis acid concentrate according to claim 20, wherein said prescribed volume is about 8 gallons of water.

22. A method of making an acid concentrate for dilution with water and a bicarbonate concentrate to produce a dialysate, comprising:
   (a) providing a powder component consisting essentially of at least one of sodium chloride and dextrose;
   (b) providing a liquid component comprising at least one of: potassium chloride, magnesium chloride, calcium chloride, dextrose, sodium chloride and an acid; and
   (c) adding said powder component and said liquid component to a prescribed volume of water, thereby to produce said acid concentrate as a solution.

23. A method as in claim 22, wherein the liquid component includes an acid selected from the group consisting of: lactic acid, acetic acid and citric acid.

24. A method as in claim 22, wherein the liquid component is between about one cup and about 2½ gallons.

25. A method as in claim 24, wherein the volume of the liquid component is about one gallon.

26. A method as in claim 22, wherein the prescribed volume of water is between about 0.5–20 gallons.

27. A method as in claim 26, wherein said prescribed volume is about 6–12 gallons of water.

28. A kit for selectively formulating an acid concentrate having any one of a plurality of formulas for subsequent dilution with water and a bicarbonate concentrate to produce a dialysate, comprising:

a plurality of containers of a powdered component, said powdered component in each said container being the same and consisting essentially of a predetermined amount of at least one of sodium chloride and dextrose; and a plurality of containers of liquid component, each said liquid component comprising at least one of: potassium chloride, magnesium chloride, calcium chloride, dextrose, sodium chloride and an acid, the liquid component in at least two said containers being of a different composition;

wherein a mixture of the contents of one of said containers of liquid component, the contents of at least one of said containers of powder component, and a prescribed volume of water produces an acid concentrate of one of the plurality of formulas.

29. The kit of claim 28, wherein the liquid component includes an acid selected from the group consisting of: lactic acid, acetic acid and citric acid.

30. The kit of claim 28, wherein a whole number multiple of said predetermined amount of sodium chloride is the amount of sodium chloride required to formulate a one of said plurality of formulas having a least amount of sodium chloride of said plurality of formulas.

31. The kit of claim 28, wherein a whole number multiple of said predetermined amount of dextrose is the amount of dextrose required to formulate a one of said plurality of formulas having a least amount of dextrose of said plurality of formulas.

32. A hemodialysis acid concentrate as in claim 1, consisting essentially of said powder component and said liquid component before mixing with water.

* * * * *

UNITED STATES PATENT AND TRADEMARK OFFICE
CERTIFICATE OF CORRECTION

PATENT NO.    : 6,251,437 B1
DATED         : June 26, 2001
INVENTOR(S)   : Fischbach, LeRoy J.

It is certified that error appears in the above-identified patent and that said Letters Patent is hereby corrected as shown below:

<u>Column 21,</u>
Line 49, delete "A hemodialysis concentrate" and substitute -- A hemodialysis acid concentrate -- therefor.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,251,437 B1
DATED        : June 26, 2001
INVENTOR(S)  : Fischbach, LeRoy J.

It is certified that error appears in the above-identified patent and that said Letters Patent is hereby corrected as shown below:

Columns 15, 16, 17 and 18, delete tables 13, 14, 15 and 16 and substitute the following tables therefore:

TABLE 13

SB-1020

| Material | Desired Final Conc. (gm/L) | Desired Starting Vol. Gallons | Material | Solids (gm) | Liquid Quart (gm) |
|---|---|---|---|---|---|
| NaCl | 172.2 | - | NaCl | 633. | - |
| CaCl(2) | 6.768 | - | CaCl(2) | - | 24.9003 |
| KCl | 5.492 | - | KCl | - | 20.2058 |
| MgCl(2) | 3.744 | - | MgCl(2) | - | 13.7747 |
| Acetic Acid | 8.847 | - | Acetic Acid | - | 32.5493 |
| Dextrose | 73.66 | - | Dextrose | 271. | - |
| Water | | 0.6 | | | |

Quantities Needed for Desired Starting Volume

| Material | Solids (lbs) | Liquid Quart (lbs) |
|---|---|---|
| NaCl | 1.40 | - |
| CaCl(2) | - | 0.05 |
| KCl | - | 0.04 |
| MgCl(2) | - | 0.03 |
| Acetic Acid | - | 0.07 |
| Dextrose | 0.06 | - |
| Total Wt. | 1.99 | 0.20 |

Total Final Vol.   0.9733 Gallons

UNITED STATES PATENT AND TRADEMARK OFFICE
CERTIFICATE OF CORRECTION

PATENT NO. : 6,251,437 B1
DATED : June 26, 2001
INVENTOR(S) : Fischbach, LeRoy J.

It is certified that error appears in the above-identified patent and that said Letters Patent is hereby corrected as shown below:

TABLE 14

SB-1080

| Material | Desired Final Conc. (gm/L) | Desired Starting Vol. Gallons | Material | Solids (gm) | Liquid Quart (gm) |
|---|---|---|---|---|---|
| NaCl | 174.2 | - | NaCl | 641.5830 | - |
| CaCl(2) | 8.122 | - | CaCl(2) | - | 29.9135 |
| KCl | 2.746 | - | KCl | - | 10.1136 |
| MgCl(2) | 3.744 | - | MgCl(2) | - | 13.7892 |
| Acetic Acid | 8.847 | - | Acetic Acid | - | 32.5837 |
| Dextrose | 73.66 | - | Dextrose | 271.2917 | - |
| Water | - | 0.6 | | | |

Quantities Needed for Desired Starting Volume

| Material | Solids (lbs) | Liquid Quart (lbs) |
|---|---|---|
| NaCl | 1.41 | - |
| CaCl(2) | - | 0.07 |
| KCl | - | 0.02 |
| MgCl(2) | - | 0.03 |
| Acetic Acid | - | 0.07 |
| Dextrose | 0.06 | - |
| Total Wt. | 2.01 | 0.19 |

Total Final Vol. 0.9743 Gallons

UNITED STATES PATENT AND TRADEMARK OFFICE
CERTIFICATE OF CORRECTION

PATENT NO. : 6,251,437 B1
DATED : June 26, 2001
INVENTOR(S) : Fischbach, LeRoy J.

It is certified that error appears in the above-identified patent and that said Letters Patent is hereby corrected as shown below:

TABLE 15

SB-100

| Material | Desired Final Conc. (gm/L) | Desired Starting Vol. Gallons | Material | Solids (gm) | Liquid Quart (gm) |
|---|---|---|---|---|---|
| NaCl | 268.2 | - | NaCl | 10756.7997 | 339.2529 |
| CaCl(2) | 9.924 | - | CaCl(2) | - | 410.5788 |
| KCl | 5.033 | - | KCl | - | 208.2268 |
| MgCl(2) | 4.574 | - | MgCl(2) | - | 189.2369 |
| Acetic Acid | 10.8 | - | Acetic Acid | - | 446.8209 |
| Dextrose | 90 | - | Dextrose | 3723.5076 | |
| Water | - | 8 | | | |

Quantities Needed for Desired Starting Volume

Total Final Vol. 41.3723 Liters

| Material | Solids (lbs) | Liquid Quart (lbs) |
|---|---|---|
| NaCl | 23.69 | 0.75 |
| CaCl(2) | - | 0.90 |
| KCl | - | 0.46 |
| MgCl(2) | - | 0.42 |
| Acetic Acid | - | 0.98 |
| Dextrose | 8.20 | - |
| Total Wt. | 31.89 | 3.51 |

Quantities Needed for Desired Starting Volume

STANDARD #1--45X
SODIUM FROM POWDER = 260 gm/l
SODIUM FROM LIQUID = 8.2 gm/l

Total Final Vol. 10.9451 Gallons

UNITED STATES PATENT AND TRADEMARK OFFICE
CERTIFICATE OF CORRECTION

PATENT NO. : 6,251,437 B1
DATED : June 26, 2001
INVENTOR(S) : Fischbach, LeRoy J.

It is certified that error appears in the above-identified patent and that said Letters Patent is hereby corrected as shown below:

TABLE 16

SB-119

| Material | Desired Final Conc. (gm/L) | Desired Starting Vol. Gallons | Material | Solids (gm) | Liquid Quart (gm) |
|---|---|---|---|---|---|
| NaCl | 263 | - | NaCl | 10756.7997 | 124.1169 |
| CaCl(2) | 9.9 | - | CaCl(2) | - | 409.5858 |
| KCl | 3.4 | - | KCl | - | 140.6658 |
| MgCl(2) | 3.4 | - | MgCl(2) | - | 140.6658 |
| Acetic Acid | 10.8 | - | Acetic Acid | - | 446.8209 |
| Dextrose | 90 | - | Dextrose | 3723.5076 | |
| Water | - | 8 | | | |

Total Final Vol.   41.3723   Liters

Quantities Needed for Desired Starting Volume

| Material | Solids (lbs) | Liquid Quart (lbs) |
|---|---|---|
| NaCl | 23.69 | 0.27 |
| CaCl(2) | - | 0.90 |
| KCl | - | 0.31 |
| MgCl(2) | - | 0.31 |
| Acetic Acid | - | 0.98 |
| Dextrose | 8.20 | - |
| Total Wt. | 31.89 | 2.78 |

STANDARD #1-45X
SODIUM FROM POWDER = 260 gm/l
SODIUM FROM LIQUID = 3 gm/l

Total Final Vol.   10.9451 Gallons

Signed and Sealed this

Twenty-sixth Day of August, 2003

JAMES E. ROGAN
*Director of the United States Patent and Trademark Office*